(12) United States Patent
Wildemeersch

(10) Patent No.: US 7,080,647 B2
(45) Date of Patent: Jul. 25, 2006

(54) T-SHAPED INTRA-UTERINE DEVICE AND METHOD FOR THE PRODUCTION THEREOF

(76) Inventor: Dirk Wildemeersch, Vossenhul 8, Knokke-Heist (BE) B-8301

( * ) Notice: Subject to any disclaimer, the term of this patent is extended or adjusted under 35 U.S.C. 154(b) by 0 days.

(21) Appl. No.: 10/504,219

(22) PCT Filed: Feb. 12, 2003

(86) PCT No.: PCT/EP03/00023

§ 371 (c)(1),
(2), (4) Date: Mar. 10, 2005

(87) PCT Pub. No.: WO03/068117

PCT Pub. Date: Aug. 21, 2003

(65) Prior Publication Data

US 2005/0178391 A1    Aug. 18, 2005

(30) Foreign Application Priority Data

Feb. 12, 2002    (BE) .................................. 2002/0088

(51) Int. Cl.
*A61F 6/06* (2006.01)
(52) U.S. Cl. ........................................ 128/833; 128/830
(58) Field of Classification Search ................ 128/833, 128/832, 831, 830
See application file for complete search history.

(56) References Cited

OTHER PUBLICATIONS

Lehtinen, Device for the release of an active agent, Jan. 18, 1996, International Publication No. WO, 96/01092.*

* cited by examiner

*Primary Examiner*—Henry Bennett
*Assistant Examiner*—Camtu Nguyen
(74) *Attorney, Agent, or Firm*—Armstrong, Kratz, Quintos, Hanson & Brooks, LLP

(57) ABSTRACT

A T-shaped intrauterine device includes a longitudinal branch constituting a body of the T, to the upper higher of which is connected a transversal stem constituting the arms of the T. The body of the T is made up of a fiber that releases an active substance. The fiber constituting the body of the T presents a transverse channel on its upper part. The arms are inserted by force into the channel to form two equal arms on opposite side of the body.

The stem forming the arms presents a curved form so that a wedging force exercised by the body on the stem is such that the latter is usually held in the channel in a position where the arms are oriented downwards of the body, while it is allowed to pivot in the channel until the arms are oriented upwards of the body under the effect of constraint exercised on the arms at the time of the extraction from the womb by an extraction wire of the device.

4 Claims, 1 Drawing Sheet

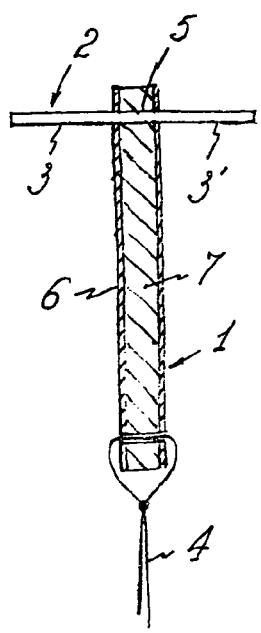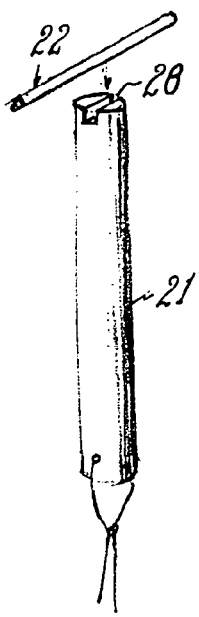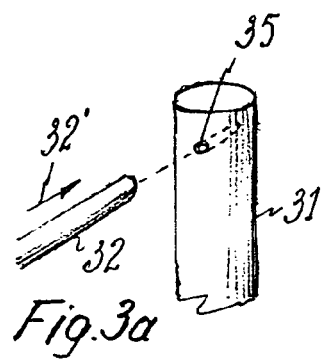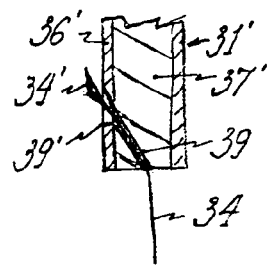
Fig. 1  Fig. 2  Fig. 3a  Fig. 3b
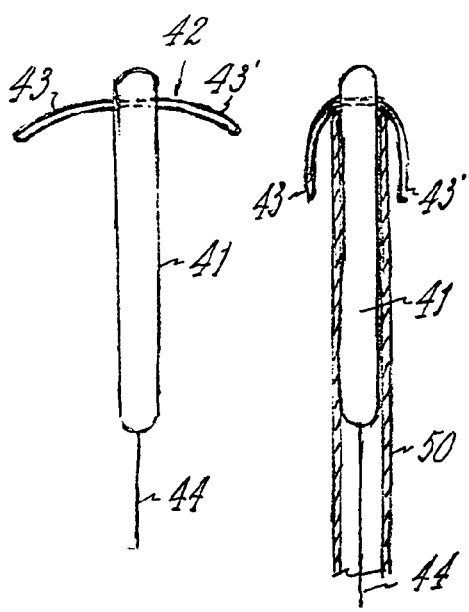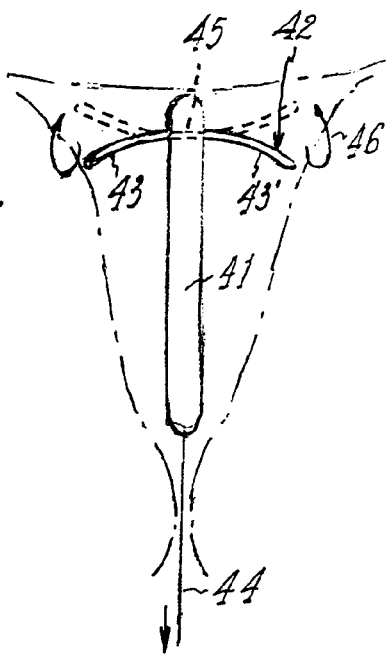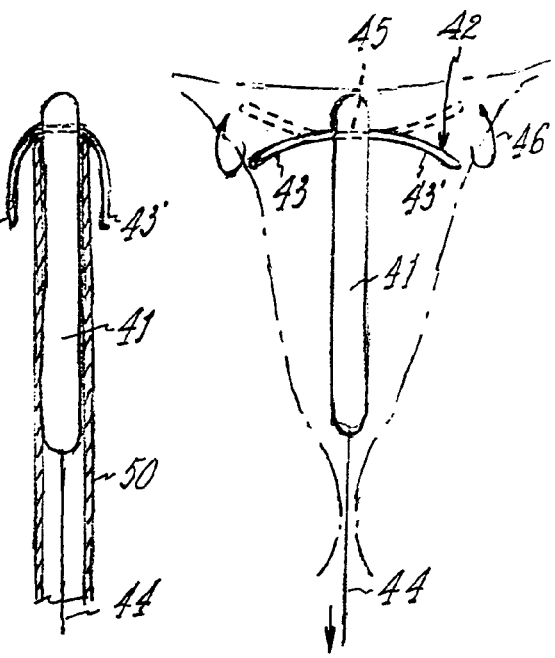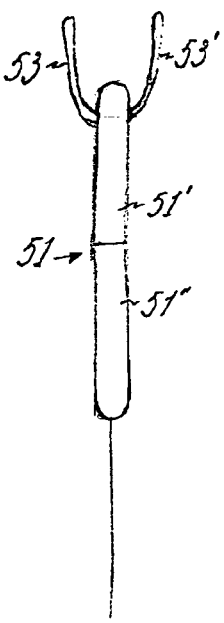
Fig. 4a  Fig. 4b  Fig. 4c  Fig. 5
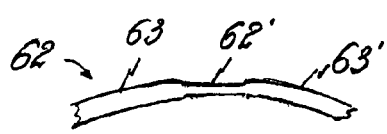
Fig. 6

T-SHAPED INTRA-UTERINE DEVICE AND METHOD FOR THE PRODUCTION THEREOF

The object of this invention is an intra-uterine device of the T-shaped type. It also has as an object the manufacturing process of this type of intra-uterine device.

In particular, the object of the invention is a new concept of intra-uterine device and its particularly inexpensive production. The device adopts the conventional form of a T and allows the release of at least one active substance, while it is capable of-containing a larger quantity of active substance than the known T-shaped devices of the same size, and thus presents, in terms of active substance release, a longer duration of action.

T-shaped intra-uterine devices have been known for some time. They are made of a single piece in moulded material and in general carry an added element on at least one of the arms for releasing an active substance, In the field of T-shaped intra-uterine devices that release active substances such as steroids, the production of a device that liberates the steroids in the form of a fibre made up of a porous membrane surrounding a nucleus containing the active substance is also known.

The production, with the aid of such fibres, of T-shaped intra-uterine devices in the form of a fibre joined to a wire equipped with means to attach to the wall of the womb has already been proposed. Said T-shaped devices, if they prove effective, are however relatively difficult to put into operation by an inexperienced person because of their attachment to the wall of the womb.

The use of steroids in conventional devices, in particular T-shaped intra-uterine devices of the type described above, has already been proposed either by winding-up, as with metallic filaments, a flexible fibre that releases the steroids (patent application PCT WO 00/67684), on at least one of the arms of the "T", or by forming in the "T" the cavities intended to receive the active material (EP 0117163), or even by providing a capsule containing the active material on one of the arms of the "T". These different embodiments, besides the fact that they involve a relatively complicated and expensive manufacturing process, produce rather bulky or cumbersome devices whose introduction into the womb is not easy in particular with young women who still have not had any children. They are also limited in terms of the quantity of active substance that they are capable of receiving, and thus in terms of their duration of action.

The purpose of the present invention is to avoid these various drawbacks by providing a less cumbersome intrauterine device, capable of containing a large quantity of active material, the device being inexpensive to manufacture. The device according to the invention allows the use of an extremely reduced section insertion device and requires little manipulation for insertion.

This purpose is reached by providing a T-shaped intrauterine device, including a longitudinal branch constituting the body of the T, the superior part of which is linked to a transversal branch constituting the arm of the T, an extraction wire being fixed to the lower part of the body of the T, characterized in that at least the body of the T is made up of a fibre that releases an active substance, and in that the arms are curved downward relative to the body.

According to other features of the device of the invention:
the fibre constituting the body of the T is provided with a transverse channel at its upper part, and the arms are made up of a stem having a section lower than the one of the fibre but higher than that the one of the channel, inserted forcibly into said channel to form two equal arms on both sides of the body, the stem forming the arms presents a curved form and the wedging force exercised by the body on the stem is such that the latter is usually retained in the channel in the position where it has been introduced, that is to say a position where the arms are oriented downwards of the body, while it is permitted to pivot in the channel until the arms are oriented upwards of the body under the effect of the constraints exercised on the arm during the extraction process of the device from the womb, the body of the T presents a cavity on its upper part in which the stem constituting the arm is housed, and in which the stem is attached to the body by gluing, the body is constituted by the end-to-end assembly of different sections of fibres, each releasing a different active material, the stem constituting the arms is also made up of a fibre that releases an active substance.

A manufacturing process for a T-shaped intrauterine device according to the invention consists in producing a fibre that releases the section-specific steroids and with release characteristics corresponding to said section and to the release characteristics as desired for the body of the intrauterine device, cutting this fibre into sections of a length corresponding to the length desired for part of the body of the intrauterine device that it constitutes, in forming a channel on the upper part of a section constituting the body of the intrauterine device to receive the stem constituting the arms and in attaching the body to the stem to the right of this channel.

According to other features of the process:
the channel intended to receive the arm on the upper part of the body may be formed by drilling and the stem constituting the arm is introduced by force into said channel the channel intended to receive the arms on the upper part of the body may be formed by grooving, the stem constituting the arms is introduced there and is held there by gluing.

for the production of an intrauterine device that releases several active substances, various fibres are cut, each releasing one of the active substances according to the characteristics desired, the sections of fibre are then assembled end to end by gluing, in the desired order, in order to form the body of the intrauterine device.

Finally, a kit for the positioning of an intrauterine device according to the invention is characterized in that it is made up, under sterile packaging, of an inserter made up of a tube with an internal diameter equal or slightly greater than the external diameter of said T-shaped body, in which the body of the T-shaped intrauterine device is housed.

The invention will be better understood in view of the description and the annexed Figures which represent, only as in an exemplative way, different embodiments of the invention in which:

FIG. 1 represents, partially in section, an embodiment of the invention,

FIG. 2 is a perspective view of another embodiment of the invention,

FIGS. 3a and 3b are a view in detail, enlarged, respectively of a preferred attachment method of the arm of the body of the device, to the upper part of the latter, and of a preferred attachment method of the extraction wire to the body on the lower part of the said body, FIG. 4a, 4b, 4c are different views of a preferred embodiment of the invention with different arm configurations, FIG. 5 is a view of an embodiment of the invention similar to that illustrated in FIGS. 4a and 4c, adapted to the release of two different active substances in the womb, the device being illustrated in yet another position of the arms, FIG. 6 is a detailed view of another embodiment of the stem constituting the arm.

As shown in FIG. 1, the intra-uterine device according to the invention is made up of a longitudinal branch constituting the body 1 of the device, a transversal branch 2 in the form of a stem constituting the arm 3, 3' of the device and of an extraction wire 4.

The body 1 is made up of a fibre that releases an active substance in the womb. In the present description "fibre" is understood to mean an element produced according to the technique of fibres known in the domain of contraception, that release for example progestagen.

Said fibres are made up of a permeable casing in the form of a membrane 6, and of a nucleus 7 containing, in a suitable support, the active substance intended to be diffused through the membrane.

The fibre used in the device of this invention is however differentiated from known fibres by the size of its transversal section that corresponds to the transversal section desired for the body 1 of the T.

Thus, the whole body assembly 1 constitutes both the active substance container as well as the diffusion surface of the active material. These two aspects ensure that the device is provided thus with a large active material substance capacity, and thus on one hand will exhibit a long duration of action and displays on the other hand an active substance diffusion surface distributed across the entire external surface of the body, which ensures the optimum distribution of the active material in the womb.

Arms 3, 3' are connected to the body 1. In the embodiment illustrated in FIG. 1 this is achieved by the introduction of the stem 2 into a channel 5 formed on the upper part of the body 1.

Another embodiment of the assembly of the arm on the body is disclosed in FIG. 2. It consists in introducing a stem 22 into a groove 28 formed on the uppermost part of the body 21 and in attaching the stem 22 of the body 21 by gluing said stem into the groove 28.

The details of the preferred embodiments of the invention are illustrated in FIGS. 3a and 3b.

More particularly, a preferred embodiment of the assembly process of the stem 32, intended to form the arms on the body 31 is disclosed in FIG. 3a in perspective. According to this embodiment the upper part of the body 31 is cut to form a channel or housing 35 whose diameter is inferior to the diameter of the stem 32, this itself being inferior to the diameter of the body 31. The stem 32 is then introduced by force into the channel 35 following the arrow 32', until the stem 32 extends approximately symmetrically on both parts of the body 31 to form the arms. The stem 32 is maintained in this way on the body 31 by wedging in the channel 35.

The symmetry of the arms is desirable, to correspond to the symmetry of the womb by ensuring the correct positioning of the active body in the womb, approximately in the axis of the latter. However, it is necessary to note that the function of the arms is to maintain the body that releases the active substance approximately in the axis of the womb, with one end near the base of the womb and the opposite end near the cervix, and that this function will be carried out even if the arms are only approximately of equal length.

FIG. 3b shows, in section, the details of a method for assembling the extraction wire 34 on the body 31. According to this embodiment the lower part of the body 31' is formed, by the membrane 36' and the nucleus 37' of a channel 39, whose part 39' formed in the membrane 36' is widened. By widening, for example by heat distortion, the end 34' of the wire 34 and by inserting the wire 34 in the channel 39 until its widened end 34' the widened part 39' of the channel 39 is blocked. This embodiment allows the retaining device of the extraction wire 34' to be imbedded completely in the body 31', and thus to limit strictly the size of the latter to the dimensions of its transversal section.

FIGS. 4a, 4b and 4c are views from various positions of the same preferred embodiment of the invention.

FIG. 4a shows the intrauterine device in its normal position of use. This device is made up of a body 41 to the upper part of which has been inserted, in a channel such as that disclosed in FIG. 3a, a curved stem forming the arms 43, 43', this curved stem being held in the channel in a position where the arms 43, 43' are directed downwards of the body 41. An extraction wire 44 is held on the lower part of the body 41 in the way illustrated in FIG. 3b.

FIG. 4b shows the intrauterine device, with its inserter 50, which is presented in the form of a tube in which the body 41 is pushed to the level of the arms 43, 43' and in which the extraction wire 44 also passes. In this Figure the arms 43, 43' are represented folded along the inserter 50, in the position that they adopt during their passage through the cervix, under the effect of the effort of the introduction process.

It should be noted here that, according to this preferred embodiment of this invention, only the T-shaped body is retained in the inserter, while the arms remain on the exterior of the inserter and curve along the latter during their passage through the cervix. This allows an important reduction in the section of the inserter used, in comparison with the majority of conventional insertion devices of T-shaped intra-uterine devices, in which the arms of the T, due to their rigidity, are folded into the inserter that results in insertion devices with a large section. In these known conventional devices, the fact that the T is integrally contained in the inserter also demands the use of a pushing device to extract the coil from the inserter tube. On the contrary, according to the illustrated embodiment of this invention, the small section of the stem 42 constituting the arms 43, 43' provides the latter with sufficient elasticity to bend along the inserter during the passage through the cervix and thereafter to resume their normal position in the womb. Once the arms 43, 43' have resumed their unfolded position in the womb they maintain by themselves, due to their contact with the walls of the womb, a holding force allowing the sliding of the body 41 out of the inserter 50 during the withdrawal process of the latter.

The reduction of the number of operations during the insertion ensures on one hand a reduction of the risk of bacterial contamination, and on the other hand a simplification of the insertion procedure, while the reduction of the period during which the arms are folded (limited to the passage through the cervix) favours an almost instantaneous return of the arms to their initial position and avoids all risk of permanent deformation capable of causing the expulsion of an intrauterine device.

Finally FIG. 4c shows the same intrauterine device in place in the womb represented in centre lines. At the end of the introduction process, the arms 43, 43' resume the position represented in the centre lines, which they maintain for the duration period of the intrauterine device, in the same way as when they are submitted to constraints resulting from the movement of the womb. On the contrary, under the effect of greater effort, such as that exerted by the walls of the womb on the end of the arm 43, 43' when traction is exerted on the wire 44, the arms pivot in their channel 45 as indicated by the arrows 46, until a position of 180° to the first is adopted, that is to say with the arm curving upwards, which facilitates the extraction of the device from the womb. As an example, the wedging force of the arms will be such as to allow their rotation in the womb by 5 Newtons of traction exercised on the traction wire.

FIG. 5 shows another embodiment of a device of the invention, designed to deliver two different active substances into the womb. For this purpose, the body 51 is made from two different fibre segments 51', 51", each obtained from a fibre containing the desired active substance. The segments 51', 51" are assembled end to end by gluing. The arms 53, 53' are represented in the positions that they occupy at the time of the extraction of the device from the womb, after rotation as shown in FIG. 4c, and being overlapped by the extraction effort at the time of the passage through the cervix.

Finally, FIG. 6 shows a possible embodiment of a stem 62 intended to form the arms 63, 63' of an intrauterine device according to the invention. According to this embodiment the stem 62 shows a deformation 62' in its centre intended to cooperate with the channel (not represented) formed in the body of the device. The diameter of the stem 62 where the deformation is located will preferably be equal or slightly lower than the diameter of the channel, and the length of the deformation corresponds approximately to the length of the channel, in order to facilitate the rotation of the arms, while preventing any noticeable lateral displacement of the arm in relation to the channel.

The fibre or section of fibre making up the body (1; 21; 31; 41) can be opened at its upper and lower ends, in the sense that the nucleus (7) containing the active substance can be uncovered there, or exposed. The release rate of active material by the uncovered nucleus 7 is higher than the release rate through the porous membrane 6, since the latter carries out a control function in this respect. This can be advantageous when one wishes, for example, to deliver more active substance into the base region and into the cervix region.

The fibre or section of fibre making up the body (1; 21; 31; 41) can also be closed at its upper and lower ends, which can be obtained, for example by pinching off the end sections, possibly with heat supply to ensure a connection or at least partial closure by welding of the lips of the membrane 6, at the ends, in such a way as to produce a fibre that ensures an approximately uniform diffusion over its entire surface.

With regard to the size of the intrauterine device of the invention, the latter are advantageously within the following intervals:

length of the stem (2; 22; 32; 42) constituting the arms: 24–32 mm
diameter of the stem (2; 22; 32; 42) constituting the arms: 1–2 mm
length of the body (1; 21; 31; 41; 51): 20–40 mm
diameter of the body (1; 21; 31; 41; 51): 1,8–3,0 mm
force necessary to rotate the arms: 1–10 Newton According to a preferred embodiment, the sizes are as follows:

length of the stem (2; 22; 32; 42) constituting the arms: ±28 mm
diameter the stem (2; 22; 32; 42) constituting the arms: ±1,5 mm
length of the body (1; 21; 31; 41; 51): ±30 mm
diameter of the body (1; 21; 31; 41; 51): ±2,4 mm
force necessary to rotate the arms: ±5Newton A device presenting dimensions according to the preferred embodiment, used as contraceptive device and containing levenorgestrel as an active material will have a calculated active duration of action of approximately 10 years, with a levenorgestrel release rate of 14–20 µg/day.

As a comparison, the T-shaped intra-uterine devices of the rolled-up fibre type or of the capsule type, as discussed in the introductory part, show in the same conditions a calculated active duration of action in the region of 1 to a maximum of 5 years.

As it is possible to ascertain from reading the description above as well as the annexed Figures, according to the invention a T-shaped intrauterine device has been achieved that combines the advantages associated with this kind of device (for example ease of positioning, reduced manipulation, and good positioning in the womb), and those of a known fibre type (active material quantity, and duration of action), the assembly being of extremely reduced dimensions.

According to the invention, this is obtained by connecting in the form of an arm, a stem that can be extremely fine (1 mm), and will generally be made of synthetic material, on a known fibre structure, forming the T-shaped body of a device.

In the intrauterine device of the invention, the fibre reservoir of active substance has a section superior to the ones of the fibres used up to now, in order to ensure a greater active material storage capacity and also to give the device greater rigidity.

Although it has not been described previously, it is obvious that the stem constituting the arms can also be made up of a fibre of the same structure as the body, impregnated with an active substance that may or may not be different to that contained in the body. This allows a further increase in the storage capacity of the device in active substance and also the substance diffusion rate in the upper part of the womb. When the ends of the fibre forming the arms are "open" in the above-mentioned way (uncovered or exposed impregnated nucleus), the diffusion rate will in particular be strengthened in the direction of the tubes, which can prove favourable.

The invention claimed is:

1. A T-shaped intrauterine device adapted to be used by a human being, comprising a body of the T, a transversal stem connected to an upper part of the body on the T and constituting arms of the T, an extraction wire being fixed to a lower part of the body of the T, wherein at least the body of the T is made up of a fibre that releases an active substance, and wherein:
   the fibre constituting the body of the T presents a transverse channel on its upper part, the stem, with a section inferior to that of the fibre but superior to that of the channel, being insertable by force into said channel to form two equal arms on opposite sides of the body and wherein;
   the stem forming the arms presents a curved form so that a wedging force exercised by the body on the stem is such that the latter is held in the channel in the position where it has been introduced in the womb, that is to say a position where the arms are oriented downwards of the body, while it is allowed to pivot in the channel until the arms are oriented upwards of the body under the effect of constraint exercised on the arms at the time of the extraction from the womb by said extraction wire of the device.

2. Device according to claim 1, wherein the body is constituted by the end to end assembly of different fibre sections, each releasing a different active substance.

3. Device according to claim 1, wherein the stem constituting the arm is also made up of a fibre that releases an active substance.

4. Kit for the positioning of an intrauterine device according to claim 1, comprising, under sterile packaging, an inserter made up of a tube, with an internal diameter equal to or slightly higher than the external diameter of said T-shaped body, in which the T-shaped body of the intrauterine device is housed.

* * * * *